(12) United States Patent
Fugh-Berman (10) Patent No.: US 10,610,494 B2
(45) Date of Patent: Apr. 7, 2020

(54) MINT MASK AND METHODS OF USE THEREOF

(71) Applicant: Georgetown University, Washington, DC (US)

(72) Inventor: Adriane Fugh-Berman, Washington, DC (US)

(73) Assignee: GEORGETOWN UNIVERSITY, Washington, DC (US)

( * ) Notice: Subject to any disclaimer, the term of this patent is extended or adjusted under 35 U.S.C. 154(b) by 274 days.

(21) Appl. No.: 15/689,332

(22) Filed: Aug. 29, 2017

(65) Prior Publication Data

US 2018/0055785 A1 Mar. 1, 2018

Related U.S. Application Data (60) Provisional application No. 62/381,270, filed on Aug. 30, 2016.

(51) Int. Cl.

| | |
|---|---|
| *A61K 36/534* | (2006.01) |
| *A61K 31/045* | (2006.01) |
| *A61K 9/00* | (2006.01) |
| *A61M 16/06* | (2006.01) |
| *A61M 16/00* | (2006.01) |
| *A61M 15/08* | (2006.01) |

(52) U.S. Cl.
CPC .......... *A61K 31/045* (2013.01); *A61K 9/0073* (2013.01); *A61K 36/534* (2013.01); *A61M 15/08* (2013.01); *A61M 16/0045* (2013.01); *A61M 16/06* (2013.01)

(58) Field of Classification Search
CPC ................................... A61K 36/534
See application file for complete search history.

(56) References Cited

U.S. PATENT DOCUMENTS

| | | | |
|---|---|---|---|
| 2009/0050144 A1* | 2/2009 | Pierce | A61F 5/56 128/200.24 |
| 2016/0375205 A1 | 12/2016 | Cressman | |

OTHER PUBLICATIONS

McKay et al., "A review of the bioactivity and potential health benefits of peppermint tea (*Mentha piperita* L.)," Phytotherapy Research 20:619-623, 2006.*
Banner et al. (2011) "TRP channels: emerging targets for respiratory disease," Pharmacol. Ther. 130:371-84.
Fujishiro et al. (Jun. 26, 2013) "Efficacy of spraying I-menthol solution during endoscopic treatment of early gastric cancer: a phase III, multicenter, randomized, double-blind, placebo-controlled study," J. Gastroentrol. 49:446-54.

(Continued)

*Primary Examiner* — Rosanne Kosson
(74) *Attorney, Agent, or Firm* — Lathrop GPM LLP; Alan W. Steele (57) ABSTRACT

Provided are methods and devices useful for treating a respiratory disease or disorder involving the central or upper airways. The methods and devices deliver to central or upper airways of a subject a vapor or aerosol comprising an effective amount of an active ingredient selected from the group consisting of menthol, menthone, neomenthol, isomenthol, and menthofuran. The methods are useful for treating conditions including cough, asthma, bronchitis, and allergic rhinitis.

8 Claims, 3 Drawing Sheets

(56) References Cited

OTHER PUBLICATIONS

Haidl et al. (2001) "[Does the inhalation of a 1% L-menthol solution in the premedication of fiberoptic bronchoscopy affect coughing and the sensation of dyspnea?]" Pneumologie. 55:115-9.—English abstract only.

Ito et al. (2008) "Inhibition by the cold receptor agonists menthol and icilin of airway smooth muscle contraction," Pulm. Pharmacol. Ther. 21:812-7.

Laude et al. (1994) "The antitussive effects of menthol, camphor and cineole in conscious guinea-pigs," Pulm. Pharmacol. 7:179-84.

Millqvist et al. (Dec. 23, 2012) "Inhalation of menthol reduces capsaicin cough sensitivity and influences inspiratory flows in chronic cough," Respir. Med. 107(1):433-8.

Pereira et al. (Jan. 2013) "The effect of inhaled menthol on upper airway resistance in humans: a randomized controlled crossover study," Can. Respir. J. 20:e1-4.

Prem et al. (Jul. 26, 2012) "Comparison of the effects of Buteyko and pranayama breathing techniques on quality of life in patients with asthma—a randomized controlled trial," Clin. Rehabil. 27:133-41.

Tamaoki et al. (1995) "Effect of menthol vapour on airway hyperresponsiveness in patients with mild asthma," Respr. Med. 89:503-4.

Willis et al. (2011) "Menthol attenuates respiratory irritation responses to multiple cigarette smoke irritants," FASEB J. 25:4434-44.

Wise et al. (2011) "The effect of menthol vapor on nasal sensitivity to chemical irritation," Nicotine Tob. Res. 13:989-97.

Wise et al. (2012) "Sweet taste and menthol increase cough reflex thresholds," Pulm. Pharmacol. Ther. 25:236-41.

Wright et al. (1997) "Capsaicin and neurokinin A-induced bronchoconstriction in the anaesthetised guinea-pig: evidence for a direct action of menthol on isolated bronchial smooth muscle," Br. J. Pharmacol. 121:1645-50.

Yamamoto et at. (2006) "Efficacy of peppermint oil as an antispasmodic during endoscopic retrograde cholangiopancreatography," J. Gastroenterol Hepatol. 21:1394-8.

* cited by examiner

Fig. 3

MINT MASK AND METHODS OF USE THEREOF

RELATED APPLICATION

This application claims benefit of priority to U.S. Provisional Patent Application No. 62/381,270, filed on Aug. 30, 2016, the entire content of which is incorporated herein by reference.

BACKGROUND OF THE INVENTION

Along with vanilla and chocolate, peppermint is one of the most common flavorings in the world, and it is widely used to flavor confectionery, chewing gum, desserts, oral hygiene products, and many other products. In addition to being a benign and ubiquitous flavoring, peppermint is also a potent antispasmodic phytomedicine that relaxes smooth muscles in many instances. The main constituents of volatile oil of peppermint are the cyclic terpene alcohol (−)-menthol ($C_{10}H_{20}O$, MW 156.27) (35-55%) and its stereoisomers menthone (10-40%), (+)-neomenthol (about 3%), and (+) isomenthol (3%). Menthol is the most prevalent and most studied constituent, but other components may contribute to the effect of peppermint oil.

Asthma is a common chronic lung disorder in which inflammation causes the bronchi to swell and narrow the airways, creating breathing difficulties that may range from mild to life-threatening. Symptoms include acute episodes of shortness of breath, cough, wheezing, and chest tightness lasting minutes to hours, even to days. Approximately 5 percent of the population of the United States is affected. Current treatments typically include beta-adrenergic agonists, methylxanthines, anticholinergics, and anti-inflammatory agents such as glucocorticoids. Beta-adrenergic agonists and anticholinergics typically are administered as aerosols, whereas methylxanthines and glucocorticoids are typically administered orally or intravenously; glucocorticoids are sometimes administered as aerosols.

Bronchitis is a common lung disorder associated with excessive tracheobronchial mucus production with cough with expectoration. Chronic bronchitis is a common chronic lung disorder associated with excessive tracheobronchial mucus production sufficient to cause cough with expectoration for at least three months of the year for more than two consecutive years. A subset of patients with chronic bronchitis have clinically significant airway obstruction accompanied by severe dyspnea (air hunger) and wheezing in association with inhaled irritants or during acute respiratory infections. Current treatments typically include beta-adrenergic agonists, methylxanthines, anticholinergics, and antibiotics. Beta-adrenergic agonists and anticholinergics typically are administered as aerosols, whereas methylxanthines and glucocorticoids are typically administered orally or intravenously; glucocorticoids are sometimes administered as aerosols.

A need still exists for effective, accessible treatments for these and other respiratory diseases and disorders.

SUMMARY OF THE INVENTION

The invention provides a phytomedicine delivery device and related methods useful to treat asthma, allergic rhinitis, bronchitis, respiratory infections, cough, and wheezing. The delivery device, which can be made of simple, easily obtainable, inexpensive materials, is designed to be portable, disposable, inexpensive, biodegradable, and suitable to be sold over-the-counter. In certain embodiments, the delivery device and methods of the invention comprise a simple mechanical rebreathing device and a pharmacologically active phytomedicine, volatile oil of peppermint. In certain embodiments, the device can be breath-activated. In certain embodiments, the device delivers therapeutic levels of two bronchodilating agents: menthol and related compounds from the peppermint oil, and carbon dioxide from trapped exhalations.

An aspect of the invention is a method of treating a respiratory disease or disorder involving the central airways, comprising administering to the central airways of a subject in need thereof a vapor or aerosol comprising a therapeutically effective amount of an active pharmaceutical ingredient (API) selected from the group consisting of menthol, menthone, neomenthol, isomenthol, menthofuran, and any combination thereof.

In certain embodiments, the API comprises menthol.

In certain embodiments, the API is provided as volatile oil of peppermint.

In certain embodiments, the vapor or aerosol is a vapor.

In certain embodiments, the vapor or aerosol is an aerosol.

In certain embodiments, the API is administered in conjunction with a rebreathing device.

In certain embodiments, the rebreathing device comprises a semi-porous substrate impregnated with the API.

In certain embodiments, the rebreathing device is a mask comprising a semi-porous substrate impregnated with the API, and the mask is constructed and arranged to fit over nose, mouth, or both nose and mouth of the subject.

In certain embodiments, the rebreathing device is breath-activated.

In certain embodiments, the vapor or aerosol is delivered to the central airways by inhalation by the subject.

In certain embodiments, the respiratory disease or disorder involving the central airways is bronchitis.

In certain embodiments, the respiratory disease or disorder involving the central airways is respiratory infection involving the central airways.

In certain embodiments, the method treats cough.

In certain embodiments, the method treats wheezing.

In certain embodiments, the subject is a human.

An aspect of the invention is a method of treating allergic rhinitis, comprising administering to the upper airways of a subject in need thereof a vapor or aerosol comprising a therapeutically effective amount of an API selected from the group consisting of menthol, menthone, neomenthol, isomenthol, menthofuran, and any combination thereof, wherein the API is administered in conjunction with a rebreathing device.

An aspect of the invention is a method of treating cough, comprising administering to the airways of a subject in need thereof a vapor or aerosol comprising a therapeutically effective amount of an API selected from the group consisting of menthol, menthone, neomenthol, isomenthol, menthofuran, and any combination thereof, wherein the API is administered in conjunction with a rebreathing device.

DETAILED DESCRIPTION OF THE INVENTION

Active Pharmaceutical Ingredient (API)

Figure 1:
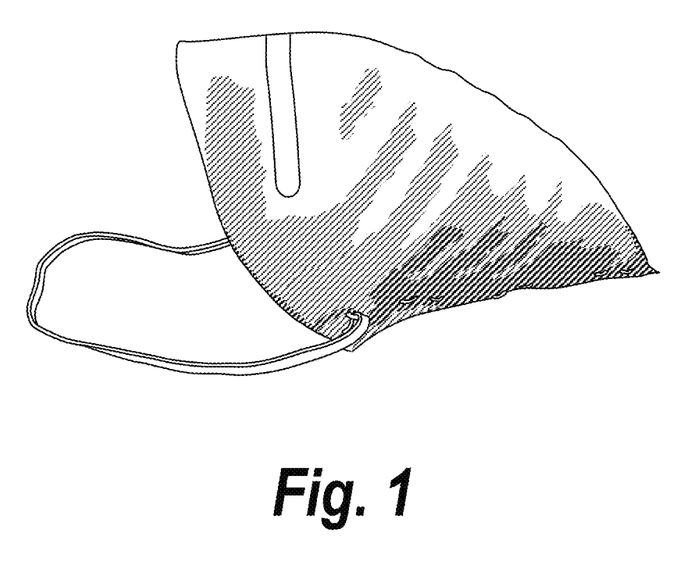
FIG. 1 depicts an embodiment of the rebreathing device.
Figure 2:
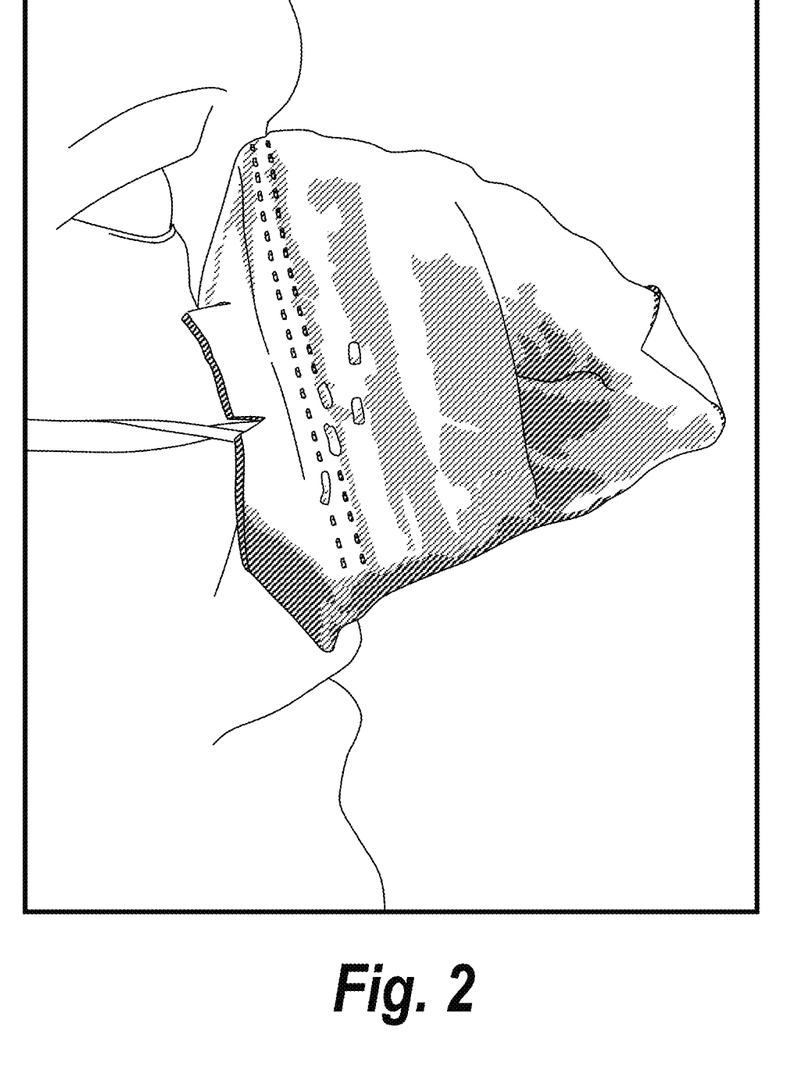
FIG. 2 depicts a subject using a rebreathing device covering the nose.
Figure 3:
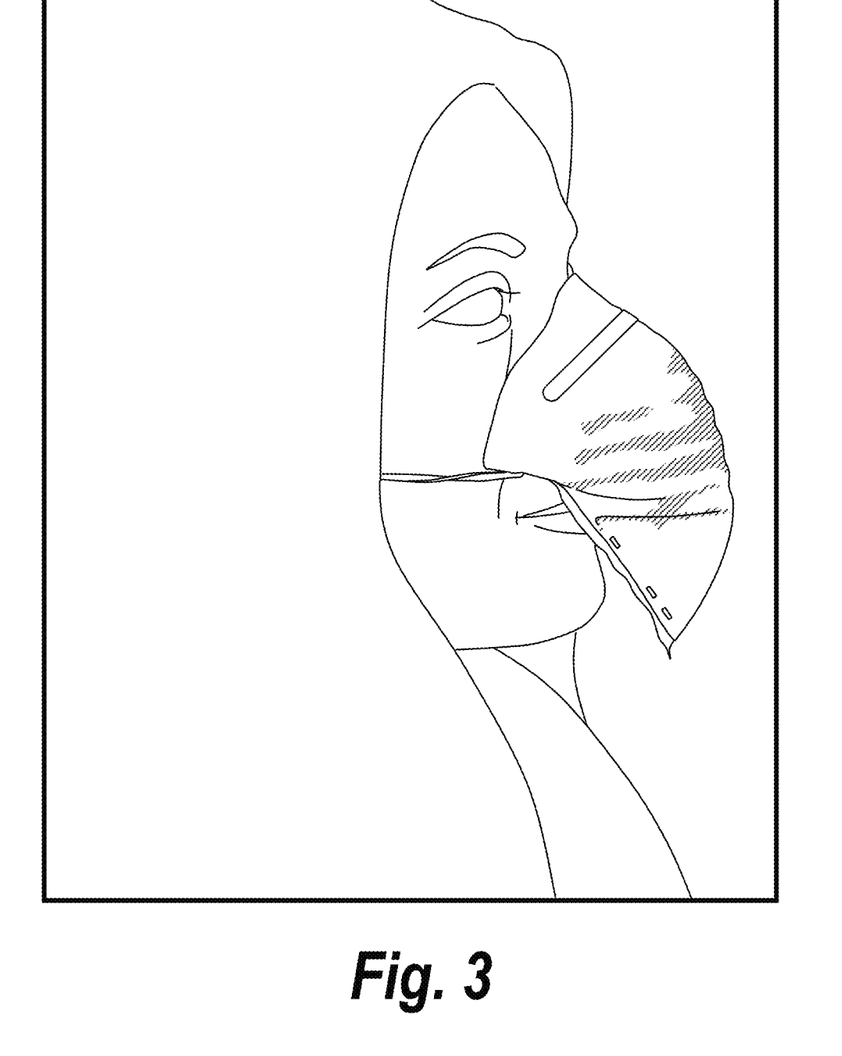
FIG. 3 depicts a subject using a rebreathing device covering both the nose and mouth.

Oil of peppermint has proven medical applications, primarily because of its antispasmodic effects on smooth muscle. Therapeutically, an oral preparation of volatile oil of peppermint oil has proven beneficial for irritable bowel syndrome in many randomized controlled trials. Khanna et al., *J. Clin. Gastroenterol.* 48: 505-12 (2014). Instilled preparations reduce spasm after colonoscopy (Shavakhi et al., *Nihon Rinsho* 68: 2126-34 (2010)), endoscopic retrograde cholangiopancreatography (ERCP; Yamamoto et at, *J. Gastroenterol Hepatol.* 21: 1394-8 (2006)), and during upper gastrointestinal endoscopy (Fujishiro et al., *J. Gastroentrol.* 49: 446-54 (2014); Hiki et al., *Dig. Endosc.* 24: 79-86 (2012)).

Few studies have been conducted on the effects of peppermint or menthol on the respiratory tract; most of these studies have focused on the nasal airway, for which results are not impressive. A recent randomized crossover trial in ten normal subjects found no effect of inhaled menthol on upper airway resistance. Pereira et al., *Can. Respir. J.* 20: e1-4 (2013).

Nevertheless, menthol is a common ingredient in cough and cold products, usually in decongestant preparations, although several studies have shown that menthol has no effect on nasal resistance. For example, menthol is an ingredient in Vicks VapoRub, an over-the-counter ointment indicated for topical use on the chest, back, and throat for cough suppression due to the common cold or on muscles and joints for minor aches and pains. Vicks VapoRub also contains camphor and eucalyptus oil, which also act as cough suppressants.

Menthol is also a common additive in cigarettes; 90% of marketed cigarettes contain menthol, including many that are not marketed as menthol cigarettes.

In guinea pigs, menthol has antitussive (cough suppressant) effects (Laude et al., *Pulm. Pharmacol.* 7: 179-84 (1994) and attenuates capsaicin- and neurokinin A-induced bronchoconstriction (Wright et al., *Br. J. Pharmacol.* 121: 1645-50 (1997)). Menthol inhibits bronchial contraction due to methacholine and high extracellular potassium; inhibition of calcium influx is important in menthol-mediated inhibition of smooth muscle contraction in airways. Ito et al., *Pulm. Pharmacol. Ther.* 21: 812-7 (2008). Other experiments have shown that menthol relaxes bronchi preconstricted with acetylcholine or potassium chloride, and has surfactant effects, lowering surface tension on bronchial surfaces. Additionally, menthol may prolong breath holding. Menthol vapor reduces reactivity to chemical irritants (Wise et al., *Nicotine Tob. Res.* 13: 989-97 (2011)) including acrolein, acetic acid, and cyclohexanone (Willis et al., *FASEB J.* 25: 4434-44 (2011)).

The mammalian transient receptor potential (TRP) cation channels are divided based on sequence homology into six categories: TRPC (canonical), TRPV (vanilloid), TRPM (melastatin), TRPA (ankyrin), TRPP (polycystin), and TRPML (mucolipin). These channels are activated by many chemical and physical stimuli and appear to be important in various respiratory diseases including asthma and chronic obstructive pulmonary disease (COPD). Banner et al., *Pharmacol. Ther.* 130: 371-84 (2011). Menthol interacts with transient receptor potential melastatin 8 (TRPM8), present in cold-sensitive sensory neurons, and transient receptor potential ankyrin 1 (TRPA1), an irritant-sensing channel.

Menthol, which is thought to have decongestant properties although it does not, is not used or marketed for bronchitis or asthma. Two of three studies have found a benefit of menthol and cough. Menthol inhalation in patients with chronic cough reduced cough sensitivity to inhaled capsaicin and had an effect on inspiratory flows. Millqvist et al., *Respire Med.* 107: 43-8 (2013). Menthol vapor and the taste of sucrose also reduced cough reflex to capsaicin challenge in another study. Wise et al., *Pulm. Pharmacol. Ther.* 25: 236-41 (2012). Another clinical study found no effect of premedication with 1% menthol inhalation on cough after fiberoptic bronchoscopy. Haidl et al., *Pneumologie* 55: 115-9 (2001).

There is only one published study on the use of menthol to treat asthma. In a study of 23 asthmatics, 4 weeks of nebulized menthol (10 mg twice daily for four weeks) decreased diurnal variation in peak expiratory flow rate (PEFR), a measure of airway excitability, reduced wheezing episodes, and reduced use of metered dose inhalers. The treatment had no effect on VC (vital capacity) or $FEV_1$ (forced expiratory volume at 1 second). Menthol may reduce airway hyperresponsiveness without changing the magnitude of airflow limitation. Tamaoki et al., *Resp. Med.* 89: 503-4 (1995).

Peppermint oil (oil of peppermint) is readily available from a number of commercial suppliers. It is volatile at room temperature.

Menthol ((1R,2S,5R)-2-Isopropyl-5-methylcyclohexanol) is readily available from a number of commercial suppliers; it is typically presented either as waxy crystals or as an oil. The main form of menthol occurring in nature is (−)-menthol, which is assigned the (1R,2S,4R) configuration. Menthol is manufactured as a single enantiomer (1R, 2S,5R-menthol; 94% ee) on the scale of 3,000 tons per year by Takasago International Corporation. The process involves an asymmetric synthesis developed by a team led by Ryōji Noyori, who won the 2001 Nobel Prize for Chemistry in recognition of his work on this process. The process begins by forming an allylic amine from myrcene, which undergoes asymmetric isomerization in the presence of a BINAP rhodium complex to give (after hydrolysis) enantiomerically pure R-citronellal. This is cyclized by a carbonyl-ene-reaction initiated by zinc bromide to isopulegol, which is then hydrogenated to give pure (1R,2S,5R)-menthol.

Rebreathing Device

Asthmatics often breathe faster as a way of compensating for airway constriction, but hyperventilation decreases carbon dioxide, thereby worsening the condition by causing lightheadedness, anxiety, and bronchoconstriction. Slow breathing not only relieves symptoms of hyperventilation, but also has a beneficial effect on asthma. Asthmatic patients can be trained in Buteyko breathing techniques, which intersperse breath holding with periods of shallow, slow breathing. Buteyko breathing has been shown to be an effective treatment for asthmatics, but it requires effort and training on the part of the subject.

Controlled breathing builds up carbon dioxide in the airways, dilating smooth muscles in the bronchi while maintaining a eucapnic state (i.e., without increasing carbon dioxide in the blood). Prem et al., *Clin. Rehabil.* 27: 133-41 (2013). A number of studies have found that Buteyko breathing techniques reduce symptoms and medication use in asthmatic patients. Compared to control and pranayama breathing, Buteyko breathing improved Asthma Control Questionnaire scores at 3 months, improved $FEV_1$, and improved $FEV_1/FVC$ (forced vital capacity). Prem et al., *Clin. Rehabil.* 27: 133-41 (2013).

A systematic review of 13 studies of asthmatic patients involving 906 participants (11 compared breathing exercise with inactive control, and two with asthma education) found improvement in quality of life in all eight studies that assessed this and an improvement (reduction) in the number of acute exacerbations in the one study that assessed this. Six of seven studies showed significant differences favoring breathing exercises for asthma symptoms. Effects on lung function were variable. A meta-analysis of the two studies assessing changes in the Asthma Quality of Life Questionnaire favored breathing exercises.

By having the user breathe into a semi-porous enclosed space, the device portion of the invention reproduces the beneficial effect of controlled breathing without requiring any effort or training on the part of the user. A semi-porous enclosed space provides plenty of oxygen and will not make a person feel air hunger; the effect is similar to breathing into a paper bag. Rebreathing also warms and humidifies air, which is helpful in preventing cold-induced asthma.

In certain embodiments, the rebreathing device is a generally cup-, cone-, or beak-shaped mask comprising a semi-porous substrate material (paper, woven or non-woven cloth, cellulose, sponge, foam, other natural fiber, or other synthetic material); for use, the semi-porous substrate material is at least partially impregnated with volatile oil of peppermint (*Mentha* x *piperita*) or of other *Mentha* species, or one or more of the major constituents of peppermint oil (e.g., menthol, menthone, or menthofuran). The mask will conformably cover the nose, or the nose and mouth, with an adjustable band, strap or tie that encircles the head or hooks over the ears to hold the mask in place. In certain embodiments, the mask will also have a flexible band or other device made of plastic, metal, or another material to improve fit over the nose. In certain embodiments, the rebreathing device is similar to or essentially the same as a commercially available dust mask. In certain embodiments, the rebreathing device is similar to or essentially the same as a commercially available surgical or medical mask.

For use, the volatile oil or constituent (API) is contacted with the device, or at least the semi-porous substrate material portion of the device, using any suitable method. In certain embodiments, the API is supplied with the mask in a container such as a small foil or plastic film or pouch with a tear-off strip that, when opened, exposes the compound. In certain embodiments, the API is provided attached to the mask in a small foil or plastic film or pouch with a tear-off strip that, when opened, exposes the compound.

The rebreathing device is constructed and arranged so that the user can breathe while wearing the device. That is, in certain embodiments, the rebreathing device is constructed and arranged so that the user can breathe through the mask.

In certain embodiments, the rebreathing device is generally a bag, inside of which is a semi-porous substrate material (paper, woven or non-woven cloth, cellulose, sponge, foam, other natural fiber, or other synthetic material); for use, the semi-porous substrate material is at least partially impregnated with volatile oil of peppermint (*Mentha* x *piperita*) or of other *Mentha* species, or one or more of the major constituents of peppermint oil (e.g., menthol, menthone, or menthofuran). For use, the volatile oil or constituent (API) is applied to the device or at least the semi-porous substrate material portion of the device using any suitable method. In certain embodiments, the API is supplied with the bag in a container such as a small foil or plastic film or pouch with a tear-off strip that, when opened, exposes the compound. The user can breathe into the bag.

Other embodiments are also contemplated by the invention. For example, in certain embodiments, the rebreathing device is generally a rigid or semi-rigid cylinder, comprising or inside of which is a semi-porous substrate material (paper, woven or non-woven cloth, cellulose, sponge, foam, other natural fiber, or other synthetic material); an open end of the cylinder is suitably sized to accommodate a user's nose or nose and mouth. For use, the semi-porous substrate material is at least partially impregnated with volatile oil of peppermint (*Mentha* x *piperita*) or of other *Mentha* species, or one or more of the major constituents of peppermint oil (e.g., menthol, menthone, or menthofuran). For use, the volatile oil or constituent (API) is contacted with the device, or at least the semi-porous substrate material portion of the device, using any suitable method.

Methods

An aspect of the invention is a method of treating a respiratory disease or disorder involving the central airways, comprising administering to the central airways of a subject in need thereof a vapor or aerosol comprising a therapeutically effective amount of an active pharmaceutical ingredient (API) selected from the group consisting of menthol, menthone, neomenthol, isomenthol, menthofuran, and any combination thereof.

As used herein, "treat" or "treating" refers to ameliorating at least one sign or symptom of a disease or disorder in a subject. In certain embodiments, the improvement can be objectively measured. For example, in treating asthma, improvement may include improvement in forced expiratory volume in one second ($FEV_1$), peak expiratory flow rate (PEFR), or both. In certain embodiments, the improvement can be subjective. In certain embodiments, "treat" or "treating" refers to fully resolving at least one sign or symptom of a disease or disorder in a subject. In certain embodiments, "treat" or "treating" refers to fully resolving a disease or disorder in a subject.

As used herein, "central airways" refers generally to the lower respiratory system, comprising larynx, trachea, bronchi, bronchioles, and alveoli. In certain embodiments, "central airways" refers to conducting airways of the lungs, i.e., trachea, bronchi, and bronchioles.

In certain embodiments, the vapor or aerosol is a vapor.
In certain embodiments, the vapor or aerosol is an aerosol.

A "respiratory disease or disorder involving central airways" refers generally to any inflammatory, allergic, irritant, or infectious disease or disorder involving central airways, or any combination thereof.

In certain embodiments, the respiratory disease or disorder involving central airways is asthma. The asthma can be allergic, cold-induced, exercise-induced, irritant-induced, or idiopathic.

In certain embodiments, the respiratory disease or disorder involving central airways is bronchitis. In certain embodiments, the bronchitis is chronic bronchitis.

In certain embodiments, the respiratory disease or disorder involving central airways is a respiratory infection involving the central airways, e.g., pneumonia or pneumonitis.

In certain embodiments, the method treats cough.
In certain embodiments, the method treats wheezing.

A "subject", as used herein, refers to a mammal. In certain embodiments, the subject is a mouse, rat, guinea pig, rabbit, cat, dog, pig, sheep, goat, cow, horse, non-human primate, or a human.

In certain embodiments, the subject is a human.

In certain embodiments, the API comprises menthol. In certain embodiments, the API consists of menthol.

In certain embodiments, the API is provided as volatile oil of peppermint.

In accordance with each of the foregoing embodiments, in certain embodiments, the API is administered in conjunction with a rebreathing device. In certain embodiments, the rebreathing device comprises a semi-porous substrate that is at least partially impregnated with the API. In certain embodiments, the rebreathing device is a mask comprising a semi-porous substrate that is at least partially impregnated with the API, and the mask is constructed and arranged to fit over the nose, mouth, or both the nose and mouth of the subject.

In certain embodiments, the rebreathing device is breath-activated. That is, the rebreathing device is activated by the subject breathing spontaneously through or into the rebreathing device, without assistance of a mechanical ventilator. The simple act of inhalation entrains the vaporized or aerosolized API and delivers the vapor or aerosol, including in particular the API, to the central airways of the subject.

Additional details and embodiments in connection with the rebreathing device are provided above.

To operate the rebreathing device, a user or subject applies the volatile oil or API to the semi-porous substrate, thereby activating the rebreathing device. In certain embodiments, for this purpose the volatile oil or API can be dissolved in alcohol or other suitable solvent. The subject dons the activated rebreathing device (e.g., mask), adjusts the fit to his or her face, and breathes using the device for a period of time sufficient to achieve a desired effect. Typically, this period of time will be about 1-30 minutes. In some embodiments, this period of time will be about 1-20 minutes. In some embodiments, this period of time will be about 1-15 minutes. In some embodiments, this period of time will be about 1-10 minutes. In some embodiments, this period of time will be about 1-5 minutes. In some embodiments, this period of time will be about 1-2 minutes. In some embodiments, this period of time will be about 2-30 minutes. In some embodiments, this period of time will be about 2-20 minutes. In some embodiments, this period of time will be about 2-15 minutes. In some embodiments, this period of time will be about 2-10 minutes. In some embodiments, this period of time will be about 2-5 minutes. In some embodiments, this period of time will be about 5-30 minutes. In some embodiments, this period of time will be about 5-20 minutes. In some embodiments, this period of time will be about 5-15 minutes. In some embodiments, this period of time will be about 5-10 minutes. In some embodiments, this period of time will be about 10-30 minutes. In some embodiments, this period of time will be about 10-20 minutes. The treatment can be repeated as needed.

In certain embodiments, the vapor or aerosol is delivered to the central airways by inhalation by the subject. For example, the subject breathes spontaneously through or into the rebreathing device, without assistance of a mechanical ventilator. The simple act of inhalation entrains the vaporized or aerosolized API and delivers the vapor or aerosol, including in particular the API, to the central airways of the subject.

An aspect of the invention is a method of treating allergic rhinitis, comprising administering to the upper airways of a subject in need thereof a vapor or aerosol comprising a therapeutically effective amount of an active pharmaceutical ingredient (API) selected from the group consisting of menthol, menthone, neomenthol, isomenthol, menthofuran, and any combination thereof, wherein the API is administered in conjunction with a rebreathing device.

Allergic rhinitis, also known as hayfever, is a common type of inflammation in the nose which occurs when the immune system reacts to allergens in the air. Symptoms typically include sneezing, rhinorrhea, post-nasal drip, nasal obstruction, and nasal, conjunctival, and pharyngeal itching.

As used herein, "upper airways" refers to the nasal cavities and pharynx.

In certain embodiments, the API comprises menthol. In certain embodiments, the API consists of menthol.

In certain embodiments, the API is provided as volatile oil of peppermint.

In certain embodiments, the vapor or aerosol is a vapor.

In certain embodiments, the vapor or aerosol is an aerosol.

In certain embodiments, the rebreathing device and its operation are as described above.

In certain embodiments, the rebreathing device is a mask comprising a semi-porous substrate impregnated with the API, and the mask is constructed and arranged to fit over nose, mouth, or both nose and mouth of the subject.

In certain embodiments, the mask is constructed and arranged to fit over the nose of the subject.

In certain embodiments, the rebreathing device is breath-activated.

In certain embodiments, the vapor or aerosol is delivered to the upper airways by inhalation by the subject.

In certain embodiments, the method treats cough.

In certain embodiments, the subject is a human.

An aspect of the invention is a method of treating cough, comprising administering to the airways of a subject in need thereof a vapor or aerosol comprising a therapeutically effective amount of an active pharmaceutical ingredient (API) selected from the group consisting of menthol, menthone, neomenthol, isomenthol, menthofuran, and any combination thereof, wherein the API is administered in conjunction with a rebreathing device.

As used herein, "airways" refers to upper, central, and/or both upper and central airways as used herein.

In certain embodiments, the API comprises menthol. In certain embodiments, the API consists of menthol.

In certain embodiments, the API is provided as volatile oil of peppermint.

In certain embodiments, the vapor or aerosol is a vapor.

In certain embodiments, the vapor or aerosol is an aerosol.

In certain embodiments, the rebreathing device and its operation are as described above.

In certain embodiments, the rebreathing device is a mask comprising a semi-porous substrate impregnated with the API, and the mask is constructed and arranged to fit over nose, mouth, or both nose and mouth of the subject.

In certain embodiments, the mask is constructed and arranged to fit over the nose of the subject.

In certain embodiments, the rebreathing device is breath-activated.

In certain embodiments, the vapor or aerosol is delivered to the airways by inhalation by the subject.

In certain embodiments, the subject is a human.

In accordance with each of the foregoing methods, a "therapeutically effective amount" as used herein refers to an amount that is sufficient to achieve a desired therapeutic effect. The therapeutically effective amount can vary depending on such factors as the particular API, the particular condition to be treated, and the age, size, and condition of the subject to be treated. The therapeutically effective amount can also vary depending on the particular arrangement of the rebreathing device and the duration of treatment.

A person of ordinary skill will be able to determine what is a therapeutically effective amount based on in vitro data, small animal data, and routine optimization.

In general, a therapeutically effective amount of the API is about 1 µg to about 100 mg per kilogram of body weight. In certain embodiments, the therapeutically effective amount of the API is about 10 µg to about 100 mg per kilogram of body weight. In certain embodiments, the therapeutically effective amount of the API is about 100 µg to about 100 mg per kilogram of body weight. In certain embodiments, the therapeutically effective amount of the API is about 1 mg to about 100 mg per kilogram of body weight. In certain embodiments, the therapeutically effective amount of the API is about 10 mg to about 100 mg per kilogram of body weight.

In certain embodiments, the therapeutically effective amount of the API is about 1 µg to about 10 mg per kilogram of body weight. In certain embodiments, the therapeutically effective amount of the API is about 10 µg to about 10 mg per kilogram of body weight. In certain embodiments, the therapeutically effective amount of the API is about 100 µg to about 10 mg per kilogram of body weight. In certain embodiments, the therapeutically effective amount of the API is about 1 mg to about 10 mg per kilogram of body weight.

In certain embodiments, the therapeutically effective amount of the API is about 1 µg to about 1 mg per kilogram of body weight. In certain embodiments, the therapeutically effective amount of the API is about 10 µg to about 1 mg per kilogram of body weight. In certain embodiments, the therapeutically effective amount of the API is about 100 µg to about 1 mg per kilogram of body weight.

In certain embodiments, the therapeutically effective amount of the API is about 1 µg to about 0.1 mg per kilogram of body weight. In certain embodiments, the therapeutically effective amount of the API is about 10 µg to about 0.1 mg per kilogram of body weight.

In certain embodiments, the therapeutically effective amount of the API is about 2.5 µg to about 100 mg per kilogram of body weight. In certain embodiments, the therapeutically effective amount of the API is about 25 µg to about 100 mg per kilogram of body weight. In certain embodiments, the therapeutically effective amount of the API is about 250 µg to about 100 mg per kilogram of body weight. In certain embodiments, the therapeutically effective amount of the API is about 2.5 mg to about 100 mg per kilogram of body weight. In certain embodiments, the therapeutically effective amount of the API is about 25 mg to about 100 mg per kilogram of body weight.

In certain embodiments, the therapeutically effective amount of the API is about 2.5 µg to about 10 mg per kilogram of body weight. In certain embodiments, the therapeutically effective amount of the API is about 25 µg to about 10 mg per kilogram of body weight. In certain embodiments, the therapeutically effective amount of the API is about 250 µg to about 10 mg per kilogram of body weight. In certain embodiments, the therapeutically effective amount of the API is about 2.5 mg to about 10 mg per kilogram of body weight.

In certain embodiments, the therapeutically effective amount of the API is about 2.5 µg to about 1 mg per kilogram of body weight. In certain embodiments, the therapeutically effective amount of the API is about 25 µg to about 1 mg per kilogram of body weight. In certain embodiments, the therapeutically effective amount of the API is about 250 µg to about 1 mg per kilogram of body weight.

In certain embodiments, the therapeutically effective amount of the API is about 2.5 µg to about 0.1 mg per kilogram of body weight. In certain embodiments, the therapeutically effective amount of the API is about 25 µg to about 0.1 mg per kilogram of body weight.

In certain embodiments, the therapeutically effective amount of the API is about 5 µg to about 100 mg per kilogram of body weight. In certain embodiments, the therapeutically effective amount of the API is about 50 µg to about 100 mg per kilogram of body weight. In certain embodiments, the therapeutically effective amount of the API is about 500 µg to about 100 mg per kilogram of body weight. In certain embodiments, the therapeutically effective amount of the API is about 5 mg to about 100 mg per kilogram of body weight. In certain embodiments, the therapeutically effective amount of the API is about 50 mg to about 100 mg per kilogram of body weight.

In certain embodiments, the therapeutically effective amount of the API is about 5 µg to about 10 mg per kilogram of body weight. In certain embodiments, the therapeutically effective amount of the API is about 50 µg to about 10 mg per kilogram of body weight. In certain embodiments, the therapeutically effective amount of the API is about 500 µg to about 10 mg per kilogram of body weight. In certain embodiments, the therapeutically effective amount of the API is about 5 mg to about 10 mg per kilogram of body weight.

In certain embodiments, the therapeutically effective amount of the API is about 5 µg to about 1 mg per kilogram of body weight. In certain embodiments, the therapeutically effective amount of the API is about 50 µg to about 1 mg per kilogram of body weight. In certain embodiments, the therapeutically effective amount of the API is about 500 µg to about 1 mg per kilogram of body weight.

In certain embodiments, the therapeutically effective amount of the API is about 5 µg to about 0.1 mg per kilogram of body weight. In certain embodiments, the therapeutically effective amount of the API is about 50 µg to about 0.1 mg per kilogram of body weight.

In certain embodiments, the therapeutically effective amount of the API is about 7.5 µg to about 100 mg per kilogram of body weight. In certain embodiments, the therapeutically effective amount of the API is about 75 µg to about 100 mg per kilogram of body weight. In certain embodiments, the therapeutically effective amount of the API is about 750 µg to about 100 mg per kilogram of body weight. In certain embodiments, the therapeutically effective amount of the API is about 7.5 mg to about 100 mg per kilogram of body weight. In certain embodiments, the therapeutically effective amount of the API is about 75 mg to about 100 mg per kilogram of body weight.

In certain embodiments, the therapeutically effective amount of the API is about 7.5 µg to about 10 mg per kilogram of body weight. In certain embodiments, the therapeutically effective amount of the API is about 75 µg to about 10 mg per kilogram of body weight. In certain embodiments, the therapeutically effective amount of the API is about 750 µg to about 10 mg per kilogram of body weight. In certain embodiments, the therapeutically effective amount of the API is about 7.5 mg to about 10 mg per kilogram of body weight.

In certain embodiments, the therapeutically effective amount of the API is about 7.5 µg to about 1 mg per kilogram of body weight. In certain embodiments, the therapeutically effective amount of the API is about 75 µg to about 1 mg per kilogram of body weight. In certain embodiments, the therapeutically effective amount of the API is about 750 µg to about 1 mg per kilogram of body weight.

In certain embodiments, the therapeutically effective amount of the API is about 7.5 µg to about 0.1 mg per mg per kilogram of body weight. In certain embodiments, the therapeutically effective amount of the API is about 75 µg to about 0.1 mg per kilogram of body weight.

The administering can be accomplished in a single dose or in a plurality of doses. In certain embodiments, the administering is accomplished in a single dose. In certain embodiments, the administering is accomplished in two doses. In certain embodiments, the administering is accomplished in three doses. In certain embodiments, the administering is accomplished in four or more doses.

The administering can be one or more times a day. In certain embodiments, the administering is once a day. In certain embodiments, the administering is twice a day. In certain embodiments, the administering is three times a day. In certain embodiments, the administering is four times a day. In various additional embodiments, the administering is 5, 6, 7, 8, 9, 10, 11, or 12 times a day. In general, the frequency and spacing of dosing can be adapted to the subject's symptoms and needs.

Kits

Also provided are kits useful in practicing the methods of the invention. In an embodiment, a kit comprises an API as disclosed herein, and a semi-porous substrate. The semi-porous substrate is suitably constructed and arranged for application of the API to the semi-porous substrate.

In an embodiment, a kit comprises an API as disclosed herein, and a rebreathing device. The rebreathing device is suitably constructed and arranged to receive the API and then deliver the API to the airways of a subject. In certain embodiments, the rebreathing device comprises a semi-porous substrate. In such embodiments, the rebreathing device is suitably constructed and arranged for application of the API to the substrate.

In certain embodiments, a kit comprises an API as disclosed herein, and a rebreathing device, wherein the rebreathing device is a mask comprising a semi-porous substrate. The rebreathing device is suitably constructed and arranged to receive the API and then deliver the API to the airways of a subject when placed over the nose or both the nose and mouth of the subject.

In each of the foregoing embodiments, the kit can further include instructions, written or otherwise, for how to use the components of the kit. For example, the instructions can direct a user how to assemble the components, e.g., how to contact the API with the rebreathing device. The instructions can also direct a user how to use the assembled, activated rebreathing device to treat the condition to be treated, e.g., how to use the assembled device to treat asthma.

The various components of the kit are typically provided in a tray or box assembly, each component optionally provided in its own compartment or packaging material. Each component optionally is provided in a sealed package, e.g., the API may be provided in a vial, pouch, or tube. A kit can include components sufficient for a single use, or it can include components sufficient for two or more uses.

I claim:

1. A method of treating asthma, comprising administering to the central airways of a subject in need thereof a vapor or aerosol comprising a therapeutically effective amount of an active pharmaceutical ingredient (API) selected from the group consisting of menthol, menthone, neomenthol, isomenthol, menthofuran, and any combination thereof, wherein the API is administered via a mask comprising a semi-porous substrate impregnated with the API, and wherein the mask is constructed and arranged to fit over the mouth, or both nose and mouth of the subset.

2. The method of claim 1, wherein the API comprises menthol.

3. The method of claim 1, wherein the API is provided as volatile oil of peppermint.

4. The method of claim 1, wherein the mask is breath-activated.

5. The method of claim 1, wherein the vapor or aerosol is delivered to the central airways by inhalation by the subject.

6. The method of claim 1, wherein the method treats coughing.

7. The method of claim 1, wherein the method treats wheezing.

8. The method of claim 1, wherein the subject is a human.

* * * * *